(12) United States Patent
Vermeiren et al.

(10) Patent No.: US 8,648,224 B2
(45) Date of Patent: *Feb. 11, 2014

(54) PROCESS FOR THE PRODUCTION OF BIO-NAPHTHA FROM COMPLEX MIXTURES OF NATURAL OCCURRING FATS AND OILS

(75) Inventors: Walter Vermeiren, Houthalen (BE); Nicolas Van Gyseghem, Brussels (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/382,308

(22) PCT Filed: Jul. 13, 2010

(86) PCT No.: PCT/EP2010/060028
§ 371 (c)(1), (2), (4) Date: Mar. 8, 2012

(87) PCT Pub. No.: WO2011/012439
PCT Pub. Date: Feb. 3, 2011

(65) Prior Publication Data
US 2012/0157728 A1    Jun. 21, 2012

(30) Foreign Application Priority Data
Jul. 27, 2009 (EP) .................. 09166485

(51) Int. Cl.
*C07C 1/20* (2006.01)

(52) U.S. Cl.
USPC ............. 585/240; 44/308; 44/629; 585/603; 585/733; 585/639

(58) Field of Classification Search
None
See application file for complete search history.

(56) References Cited

U.S. PATENT DOCUMENTS

| | | |
|---|---|---|
| 4,992,605 A | 2/1991 | Craig et al. |
| 2004/0192981 A1 | 9/2004 | Appel et al. |
| 2006/0161032 A1 | 7/2006 | Murzin et al. |
| 2008/0052983 A1 | 3/2008 | Aulich et al. |
| 2008/0308457 A1 | 12/2008 | Dindi et al. |
| 2009/0069610 A1 | 3/2009 | Roberts, IV et al. |
| 2009/0084026 A1* | 4/2009 | Miller ............... 44/308 |
| 2009/0158637 A1 | 6/2009 | McCall et al. |
| 2010/0292517 A1 | 11/2010 | Debuisschert et al. |

FOREIGN PATENT DOCUMENTS

| | | | |
|---|---|---|---|
| CN | 101343552 | * | 1/2009 |
| EP | 1396531 A2 | | 3/2004 |
| EP | 1741767 A1 | | 1/2007 |

OTHER PUBLICATIONS

Maher, et al.; "Pyrolysis of Triglyceride Materials for the Production of Renewable Fuels and Chemicals"; Bioresource Technology, Elsevier BV, GB LNKD-DOI; 10.1016/J. Biortech. 2006.10.025; vol. 98, No. 12; Mar. 19, 2007; pp. 2351-2368; XP005932842; ISSN: 0960-8524; p. 2357.

Demirbas, A.; "Biodiesel Fuels From Vegetable Oils Via Catalytic and Non-Catalytic Supercritical Alcohol Transesterifications and Other Methods: A Survey"; Energy Conversion and Management, Elsevier Science Publishers, Oxford, GB LNKD-DOI: 10.1016/S0196-8904(02)00234-0; vol. 44, No. 13; Aug. 1, 2003; pp. 2093-2109; XP004414476; ISSN: 0196-8904; pp. 2100-2101; Figure 2, Table 5.

C.C. Chang, et al.; "China's Motor Fuels From Tung Oil"; Ind. Eng. Chem.; vol. 39, No. 12; 1947; pp. 1543-1548; XP002577034.

* cited by examiner

*Primary Examiner* — Tam M Nguyen (57) ABSTRACT

A process for making a bio-naphtha and optionally bio-propane from a complex mixture of natural occurring fats & oils, wherein
said complex mixture is subjected to a refining treatment for removing the major part of non-triglyceride and non-fatty acid components, thereby obtaining refined fats & oils;

said refined fats & oils are transformed into linear or substantially linear paraffin's as the bio-naphtha by an hydrodeoxygenation or from said refined fats & oils are obtained fatty acids that are transformed into linear or substantially linear paraffin's as the bio-naphtha by hydrodeoxygenation or decarboxylation of the free fatty acids or from said refined fats & oils are obtained fatty acids soaps that are transformed into linear or substantially linear paraffin's as the bio-naphtha by decarboxylation of the soaps.

13 Claims, 4 Drawing Sheets

PROCESS FOR THE PRODUCTION OF BIO-NAPHTHA FROM COMPLEX MIXTURES OF NATURAL OCCURRING FATS AND OILS

CROSS-REFERENCE TO RELATED APPLICATIONS

This application claims the benefit of PCT/EP2010/060028, filed Jul. 13, 2010, which claims priority from EP 09166485.4, filed Jul. 27, 2009.

FIELD OF THE INVENTION

The present invention relates to the production of bio-naphtha in an integrated bio-refinery from complex mixtures of natural occurring fats & oils. The limited supply and increasing cost of crude oil and the need to reduce emission of fossil based carbon dioxides has prompted the search for alternative processes for producing hydrocarbon products such as bio-naphtha and bio-diesel. The bio-naphtha can be used as feedstock of conventional steamcracking. Made up of organic matter from living organisms, biomass is the world's leading renewable energy source.

BACKGROUND OF THE INVENTION

The industrial chemistry of fats & oils is a mature technology, with decades of experience and continuous improvements over current practices. Natural fats & oils consist mainly of triglycerides and to some extent of free fatty acids (FFA). Many different types of triglycerides are produced in nature, either from vegetable as from animal origin. Fatty acids in fats & oils are found esterified to glycerol (triacylglycerol). The acyl-group is a long-chain ($C_{12}$-$C_{22}$) hydrocarbon with a carboxyl-group at the end that is generally esterified with glycerol. Fats & oils are characterized by the chemical composition and structure of its fatty acid moiety. The fatty acid moiety can be saturated or contain one or more double bonds. Bulk properties of fats & oils are often specified as "saponification number", "Iodine Value", "unsaponification number". The "saponification number", which is expressed as grams of fat saponified by one mole of potassium hydroxide, is an indication of the average molecular weight and hence chain length. The "Iodine value", which is expressed as the weight percent of iodine consumed by the fat in a reaction with iodine monochloride, is an index of unsaturation.

Some typical sources of fats & oils and respective composition in fatty acids are given by way of example in Table 1.

TABLE 1

|  | Symbol | Cotton- | Coconut | Corn | Palm | Peanut | Palm | Linseed | Rice | Rape- | Olive |
|---|---|---|---|---|---|---|---|---|---|---|---|
| Saturated |  |  |  |  |  |  |  |  |  |  |  |
| Caproic | 6:0 |  | 0.4 |  | 0.2 |  |  |  |  |  |  |
| Caprylic | 8:0 |  | 7.3 |  | 3.3 |  |  |  |  |  |  |
| Capric | 10:0 |  | 6.6 |  | 3.5 |  |  |  |  |  |  |
| Lauric | 12:0 |  | 47.8 |  | 47.8 |  | 0.2 |  |  |  |  |
| Myristic | 14:0 | 0.9 | 18.1 |  | 16.3 | 0.1 | 1.1 |  | 0.4 |  | 0.02 |
| Palmitic | 16:0 | 24.7 | 8.9 | 10.9 | 8.5 | 11.6 | 44.1 | 6.0 | 19.8 | 3.9 | 10.5 |
| Margaric | 17:0 |  |  |  |  |  |  |  |  |  | 0.05 |
| Stearic | 18:0 | 2.3 | 2.7 | 1.8 | 2.4 | 3.1 | 4.4 | 2.5 | 1.9 | 1.9 | 2.6 |
| Arachidic | 20:0 | 0.1 | 0.1 |  |  | 1.5 | 0.2 | 0.5 | 0.9 | 0.6 | 0.4 |
| Behenic | 22:0 |  |  |  |  | 3.0 |  |  | 0.3 | 0.2 | 0.2 |
| Lignoceric | 24:0 |  |  |  |  | 1.0 |  |  |  | 0.2 | 0.1 |
| TOTAL |  | 28.0 | 91.9 | 22.7 | 82.0 | 20.3 | 50 | 9.0 | 23.3 | 6.8 | 13.87 |
| Unsaturated |  |  |  |  |  |  |  |  |  |  |  |
| Myristoleic | 14:1 w-5 |  |  |  |  |  |  |  |  |  |  |
| Palmitoleic | 16:1 w-7 | 0.7 |  |  |  | 0.5 |  | 0.1 | 0.2 |  | 0.6 |
| Heptadecenoic | 17:1 w-15 |  |  |  |  |  |  |  |  |  | 0.09 |
| Oleic | 18:1 w-9 | 17.6 | 6.4 | 24.2 | 15.4 | 38.0 | 37.5 | 19.0 | 42.3 | 64.1 | 76.9 |
| Linoleic | 18:2 w-6 | 53.3 | 1.6 | 58.0 | 2.4 | 41.0 | 10 | 24.1 | 31.9 | 18.7 | 7.5 |
| Linolenic | 18:3 w-3 | 0.3 |  | 0.7 |  |  |  | 47.4 | 1.2 | 9.2 | 0.6 |
| Gadolenic | 20:1 w-9 |  |  |  |  | 1.0 | 0.5 |  | 0.5 | 1.0 | 0.3 |
| TOTAL |  | 72.0 | 8.1 | 77.3 | 18.0 | 79.7 | 50 | 91 | 76.7 | 93.2 | 86.13 |
| Polyunsaturated |  |  |  |  |  |  |  |  |  |  |  |
| Ricinoleic | 18 |  |  |  |  |  |  |  |  |  |  |
| Rosin acids | — |  |  |  |  |  |  |  |  |  |  |
| % FFA |  | 0.5-0.6 | 1.0-3.5 | 1.7 | 0.1 | 0.8 | 2-14 | 2 | 5-15 | 0.5-3.8 | 0.5-3.3 |

|  |  | Soy- | Sun- | Linola | Lard | Butterfat | Tallow | Tall | Castor | Jatropha |
|---|---|---|---|---|---|---|---|---|---|---|
|  | Saturated |  |  |  |  |  |  |  |  |  |
|  | Caproic |  |  |  |  | 2 |  |  |  |  |
|  | Caprylic |  |  |  |  | 2 |  |  |  |  |
|  | Capric |  |  |  |  | 3 |  |  |  |  |
|  | Lauric |  | 0.5 |  | 0.5 | 3.5 |  |  |  |  |
|  | Myristic | 0.1 | 0.2 |  | 1.5 | 11 | 3 |  |  |  |
|  | Palmitic | 11.0 | 6.8 | 5.6 | 26 | 26 | 26 | 2 | 1.0 | 14.6 |
|  | Margaric |  |  |  | 0.5 |  | 0.5 |  |  |  |
|  | Stearic | 4.0 | 4.7 | 4.0 | 13.5 | 11 | 22.5 | 1 | 1.0 | 7.4 |

TABLE 1-continued

| | | | | | | | | | |
|---|---|---|---|---|---|---|---|---|---|
| Arachidic | 0.3 | 0.4 | | | 2 | | 0.5 | | |
| Behenic | 0.1 | | | | | | | | |
| Lignoceric | | | | | | | | | |
| TOTAL Unsaturated | 15.5 | 12.6 | 9.6 | 42.0 | 60.5 | 52.0 | 3.5 | 2.0 | 22.0 |
| Myristoleic | | | | | | 0.5 | | | |
| Palmitoleic | 0.1 | 0.1 | | 4 | 2 | 2.5 | | | 0.8 |
| Heptadecenoic | | | | 0.5 | 3 | 0.5 | | | |
| Oleic | 23.4 | 18.6 | 15.9 | 43 | 26 | 43 | 16 | 3.0 | 47.5 |
| Linoleic | 53.2 | 68.2 | 71.8 | 9 | 2.5 | 1.5 | 20 | 4.2 | 28.7 |
| Linolenic | 7.8 | 0.5 | 2.0 | 0.5 | 4 | | | 0.3 | 1.0 |
| Gadolenic | | | | 1 | | | 0.5 | | |
| TOTAL Polyunsaturated | 84.5 | 87.4 | 90.4 | 58.0 | 37.5 | 48.0 | 54.5 | 7.5 | 78.0 |
| | | | | | 2 | | 4 | | |
| Ricinoleic | | | | | | | | 89.5 | |
| Rosin acids | | | | | | | 40 | | |
| % FFA | 0.3-1.6 | 0.1-1.5 | 0.3 | 0.5 | | 5-20 | | | |

There are other potential feedstock available at this time, namely trap and sewage grease and other very high free fatty acid greases who's FFA can exceed 50%.

The main sources of fats & oils are palm and palm kernels, soybeans, rapeseed, sunflower, coconut, corn, animal fats, milk fats.

Potentially new sources of triglycerides will become available in the near future, namely those extracted from Jatropha and those produced by microalgues. These microalgues can accumulate more then 30 wt % of lipids on dry basis and they can either be cultivated in open basin, using atmospheric $CO_2$ or in closed photobioreactors. In the latter case, the required $CO_2$ can originate from the use of fossil hydrocarbons that are captured and injected into the photobioreactor. Main sources of fossil $CO_2$ are power stations, boilers used in refineries and steamcrackers furnaces used to bring hydrocarbon streams at high temperature or to supply heat of reactions in hydrocarbon transformations in refineries and steamcrackers. In particular steameracking furnaces produce a lot of $CO_2$. In order to enhance the $CO_2$ concentration in flue gases of these furnaces, techniques like oxycombustion, chemical looping or absorption of $CO_2$ can be employed. In oxycombustion, oxygen is extracted from air and this pure oxygen is used to burn hydrocarbon fuels as to obtain a stream only containing water and $CO_2$, allowing concentrating easily the $CO_2$ for storage or re-utilisation. In chemical looping, a solid material acts as oxygen-transfer agent from a re-oxidation zone where the reduced solid is re-oxidised with air into oxidised solid to a combustion zone, where the hydrocarbon fuel is burned with the oxidised solid and hence the effluent resulting from the combustion zone only contains water and $CO_2$. Absorption of $CO_2$ can be done with the help of a lean solvent that has a high preferential to absorb $CO_2$ under pressure and typically at low temperature and will release the $CO_2$ when depressurized and/or heated. Rectisol® and Selexol® are commercial available technologies to remove and concentrate $CO_2$. Other sources of $CO_2$ are the byproduct from carbohydrates fermentation into ethanol or other alcohols and the removal of excess $CO_2$ from synthesis gas made from biomass or coal gasification.

US 2007/0175795 reports the contacting of a hydrocarbon and a triglyceride to form a mixture and contacting the mixture with a hydrotreating catalyst in a fixed bed reactor under conditions sufficient to produce a reaction product containing diesel boiling range hydrocarbons. The example demonstrates that the hydrotreatment of such mixture increases the cloud point and pour point of the resulting hydrocarbon mixture.

US 2004/0230085 reports a process for producing a hydrocarbon component of biological origin, characterized in that the process comprises at least two steps, the first one of which is a hydrodeoxygenation step and the second one is an isomerisation step. The resulting products have low solidification points and high cetane number and can be used as diesel or as solvent.

US 2007/0135669 reports the manufacture of branched saturated hydrocarbons, characterized in that a feedstock comprising unsaturated fatty acids or fatty acids esters with C1-C5 alcohols, or mixture thereof, is subjected to a skeletal isomerisation step followed by a deoxygenation step. The results demonstrate that very good cloud points can be obtained.

US 2007/0039240 reports on a process for cracking tallow into diesel fuel comprising: thermally cracking the tallow in a cracking vessel at a temperature of 260-371° C., at ambient pressure and in the absence of a catalyst to yield in part cracked hydrocarbons.

U.S. Pat. No. 4,554,397 reports on a process for manufacturing olefins, comprising contacting a carboxylic acid or a carboxylic ester with a catalyst at a temperature of 200-400° C., wherein the catalyst simultaneously contains nickel and at least one metal from the group consisting of tin, germanium and lead.

It has been discovered a process to make bio-naphtha in an integrated biorefinery from all kinds of natural triglycerides or fatty acids. In said process crude fats & oils are refined, either physically or chemically, to remove substantially all non-triglyceride components and non-free fatty acids.

The use of a biofeed is a possible solution in the search of alternative raw material for the naphthacracker. Nevertheless, using this type of feed can lead to corrosion problems and excessive fouling because of oxygenates forming from the oxygen atoms in the biofeed. Also existing steamcrackers are not designed to remove high amounts of carbonoxides that would result from the steamcracking of these biofeedstock. According to the present invention, such a problem can be solved by hydrodeoxygenating/decarboxylating (or decarbonylating) this biofeed before its injection into the steam cracker. Thanks to this hydrodeoxygenation/decarboxylation (or decarbonylation), the negative effect due to the production of CO and $CO_2$ and traces of low molecular weight oxygenates (aldehydes and acids) in the steam cracker is reduced.

Another advantage is of course the production of biomonomers in the steam cracker.

BRIEF DESCRIPTION OF THE INVENTION

The subject-matter of the present invention is, in a first embodiment, a process for making a bio-naphtha from a complex mixture of natural occurring fats & oils, wherein said complex mixture is subjected to a refining treatment for removing the major part of the non-triglyceride and non-fatty acid components, thereby obtaining refined oils;

said refined fats & oils are transformed into linear or substantially linear paraffin's as the bio-naphtha by an hydrodeoxygenation or from said refined fats & oils are obtained fatty acids that are transformed into linear or substantially linear paraffin's as the bio-naphtha by hydrodeoxygenation or decarboxylation of the fatty acids or from said refined fats & oils are obtained fatty acids soaps that are transformed into linear or substantially linear paraffin's as the bio-naphtha by decarboxylation of the soaps.

In an embodiment 2 the invention is according to embodiment 1, wherein said complex mixture of natural occurring fats & oils is selected among vegetable oils and animal fats, preferentially inedible oils, highly saturated oils, waste food oils, by-products of the refining of vegetable oils, and mixtures thereof.

In an embodiment 3 the invention is according to embodiment 1 or 2, wherein said fatty acids are obtained by physical refining, including a steam distillation or vacuum distillation of fats & oils or said fatty acids are obtained by hydrolysis of triglycerides of the fats & oils or said fatty acids are obtained by acidulation of soaps.

In an embodiment 4 the invention is according to embodiment 1 or 2, wherein said fatty acid soaps are obtained by saponification of fats & oils or by the chemical refining, including neutralisation of free fatty acids, present in the fats & oils or neutralisation of fatty acids, obtained from hydrolysis of the fats & oils In an embodiment 5 the invention is according to anyone of embodiments 1 to 3, wherein said refined fats & oils are transformed into linear or substantially linear paraffins as bio-naphtha together with bio-propane by hydrodeoxygenation in the presence of hydrogen and of at least one catalyst that can be selected among Ni, Mo, Co or mixtures like NiW, NiMo, CoMo, NiCoW, NiCoMo, NiMoW and CoMoW oxides or sulphides as catalytic phase, preferably supported on high surface area carbon, alumina, silica, titania or zirconia.

In an embodiment 6 the invention is according to embodiment 5, wherein the hydrodeoxygenation is carried out at a temperature from 200 to 500° C., under a pressure from 1 MPa to 10 MPa (10 to 100 bars) and with a hydrogen to feed ratio from 100 to 2000 Nl/l.

In an embodiment 7 the invention is according to anyone of Embodiments 1 to 4, wherein said refined oils are transformed into linear or substantially linear paraffins as bio-naphtha by hydrolysis of the fats & oils into glycerol and fatty acids, removal of the glycerol or by physical refining, including a steam distillation or vacuum distillation of fats & oils or obtained by acidulation of soaps and hydrodeoxygenation or decarboxylation of the fatty acids, said hydrodeoxygenation or decarboxylation being conducted in the presence of hydrogen and of at least one catalyst that can be selected among Ni, Mo, Co or mixtures like NiW, NiMo, CoMo, NiCoW, NiCoMo, NiMoW and CoMoW oxides or sulphides as catalytic phase, preferably supported on high surface area carbon, alumina, silica, titania or zirconia or group 10 (Ni, Pt and Pd) and group 11 (Cu and Ag) metals or alloy mixtures supported on high surface area carbon, magnesia, zinc-oxide, spinels ($Mg_2Al_2O_4$, $ZnAl_2O_4$), perovskites ($BaTiO_3$, $ZnTiO_3$), calciumsilicates (like xonotlite), alumina, silica or silica-alumina's or mixtures of the latter.

In an embodiment 8 the invention is according to anyone of embodiments 1 to 4, wherein said refined oils are transformed into linear or substantially linear paraffin's as bio-naphtha by hydrolysis of the fats & oils into glycerol and fatty acids, removal of the glycerol or by physical refining, including a steam distillation or vacuum distillation of fats & oils or obtained by acidulation of soaps and decarboxylation of the fatty acids is carried out on basic oxides, like alkaline oxides, alkaline earth oxides, lanthanide oxides, zinc-oxide, spinels ($Mg_2Al_2O_4$, $ZnAl_2O_4$), perovskites ($BaTiO_3$, $ZnTiO_3$), calciumsilicates (like xonotlite), either as bulk material or dispersed on neutral or basic carriers, on basic zeolites (like alkali or alkaline earth low silica/alumina zeolites obtained by exchange or impregnation).

In an embodiment 9 the invention is according to embodiments 7 and 8, wherein the hydrodeoxygenation is carried out at a temperature from 200 to 500° C., under a pressure from 1 MPa to 10 MPa (10 to 100 bars) and with a hydrogen to feedstock ratio from 100 to 2000 Nl/l. or wherein the decarboxylation is carried out at a temperature from 100 to 550° C., under a pressure from 0.1 MPa to 10 MPa (1 to 100 bars) and with a hydrogen to feedstock ratio from 0 to 2000 Nl/l.

In an embodiment 10 the invention is according to embodiment 4, wherein the decarboxylation of the soaps is carried out at from 100 to 550° C. under pressure from 0.1 Mpa to 10 Mpa and in presence of water.

In an embodiment 11 the invention is according to embodiments 4 and 10, wherein the decarboxylation of the soaps is carried out with a water to feedstock ratio of at least 1 mole water per mole of soap.

In an embodiment 12 the invention is the Use of the bio-naphtha as obtained in the process of any one of embodiments 1 to 11, as a direct feedstock of a steamcracker, said bio-naphtha being used as such, or together with the bio-propane when produced by the process of embodiment 5, or as blended with at least a conventional feedstock selected among LPG, naphtha and gasoil, in order to obtain cracked products including bio-ethylene, bio-propylene, bio-butadiene, bio-isoprene, bio-cyclopentadiene and bio-piperylenes, bio-benzene, bio-toluene, bio-xylene and bio-gasoline, wherein in the steamcracking process the hydrocarbon feedstock is mixed with steam in a ratio of 0.3 to 0.45 kg steam per kg hydrocarbon feedstock.

In an embodiment 13 the invention is the process of embodiment 12 wherein the hydrocarbon feedstock is mixed with steam in a ratio of 0.3 to 0.4 kg steam per kg hydrocarbon feedstock.

In an embodiment 14 the invention is a process for steam cracking a feedstock as defined in embodiment 12 or 13, wherein the mixture is heated up to a temperature of 750-950° C. at a residence time of 0.05 to 0.5 seconds.

In an embodiment 15 the invention is a process for steam cracking a feedstock as defined in any one of embodiments 12 to 14, wherein the mixture is heated up to a temperature of 750-950° C. at a residence time of 0.05 to 0.15 seconds.

In an embodiment 16 the invention is the Use of the bio-naphtha as obtained in the process of any one of embodiments 1 to 11 for steamcracking such as to obtain a ethylene to methane weight ratio, resulting from the cracking of bio-naphtha, of at least 3.

By "bio-naphtha" we mean naphtha produced from renewable sources by hydrotreatment of these renewable sources. It is a hydrocarbon composition, consisting of mainly paraffin's and that can be used for the steamcracking to produce light olefins, dienes and aromatics. The molecular weight of this bio-naphtha ranges from hydrocarbons having 8 to 24 carbons, preferably from 10 to 18 carbons.

By "substantially linear paraffins", we mean a composition of paraffin's consisting of at least 90% by weight of linear paraffin's.

Said complex mixture of natural occurring fats & oils can be selected among vegetable oils and animal fats, preferentially inedible highly saturated oils, waste food oils, by-products of the refining of vegetable oils, and mixtures thereof. Specific examples of these fats & oils have been previously mentioned in the present specification.

Said refined oils, eventually still containing some free fatty acids can be transformed into linear or substantially linear paraffin's as bio-naphtha together with bio-propane by hydrodeoxygenation in the presence of hydrogen and of at least one hydrodeoxygenation catalyst. The hydrodeoxygenation catalyst can be selected among Ni, Mo, Co or mixtures like NiW, NiMo, CoMo, NiCoW, NiCoMo, NiMoW and CoMoW oxides or sulphides as catalytic active phase, preferably supported on high surface area carbon, alumina, silica, titania or zirconia or group 10 (Ni, Pt or Pd) or group 11 (Cu or Ag) metals or alloy mixtures supported on high surface area carbon, magnesia, zinc-oxide, spinels ($Mg_2Al_2O_4$, $ZnAl_2O_4$), perovskites ($BaTiO_3$, $ZnTiO_3$), calciumsilicates (like xonotlite), alumina, silica or mixtures of the latter. It is preferred that the support for the catalytic active phase exhibit low acidity, preferable neutral or basic in order to avoid hydro-isomerisation reactions that would result in branched paraffin's and cracking. The hydrodeoxygenation of the fats & oils can be carried out at a temperature from 200 to 500° C., preferably from 280 to 400° C., under a pressure from 1 MPa to 10 MPa (10 to 100 bars), for example of 6 MPa, and with a hydrogen to refined oils ratio from 100 to 2000, but preferably from 350 to 1500 for example of 600 Nl H2/l oil.

Said refined oils can also be transformed into linear or substantially linear paraffin's as bio-naphtha by producing fatty acids by (i) hydrolysis of the fats & oils into glycerol and fatty acids, removal of the glycerol, by (ii) physical refining (steam/vacuum distillation) of fats & oils or by acidulation of fatty acid soaps and subsequently hydrodeoxygenation or decarboxylation (or decarbonylation) of the fatty acids, said hydrodeoxygenation being conducted in the presence of hydrogen and of at least one hydrodeoxygenation or decarboxylation catalyst. The hydrodeoxygenation or decarboxylation catalyst can be selected among Ni, Mo, Co or mixtures like NiW, NiMo, CoMo, NiCoW, NiCoMo, NiMoW and CoMoW oxides or sulphides as catalytic phase, preferably supported on high surface area carbon, alumina, silica, titania or zirconia or group 10 (Ni, Pt or Pd) or group 11 (Cu or Ag) metals or alloy mixtures supported on high surface area carbon, magnesia, zinc-oxide, spinels ($Mg_2Al_2O_4$, $ZnAl_2O_4$), perovskites ($BaTiO_3$, $ZnTiO_3$), calciumsilicates (like xonotlite), alumina, silica or silica-alumina's or mixtures of the latter. It is preferred that the support for the catalytic active phase exhibit low acidity, preferable neutral or basic in order to avoid hydro-isomerisation reactions that would result in branched paraffin's and cracking. The hydrolysis (splitting) can be carried out in presence of steam thermally at 15 to 75 bars and at 50-300° C. or catalytically, for example with basic catalysts, like MgO, CaO, ZnO, spinels ($Mg_2Al_2O_4$, $ZnAl_2O_4$), perovskites ($BaTiO_3$, $ZnTiO_3$), calciumsilicates (like xonotlite) or basic alumina or with acidic catalysts, like sulphuric acid. Detailed information about fat & oil splitting has been published by Sonntag (Sonntag, N., J. Am. Oil. Chem. Soc., 56, p. 729, 1979 and Bailey's Industrial Oil and Fat Products, ed. F. Shahidi, 2005, John Wiley & Sons). In the Colgate-Emery process, heated liquid lipid is introduced at the bottom of a vertical tubular reactor. Heated water enters at the top. As the fats & oils rises through the descending water under pressure, a continuous zone of high water solubility in oil establishes, wherein hydrolysis occurs. Effluent from the column is recovered, fatty acids from one outlet and an aqueous glycerol stream from the other. The presence of small amounts of mineral acids, such as sulfuric acid or sulfonic acids or certain metal oxides, such as zinc or magnesium oxide, accelerates the splitting reaction. These metal oxides are true catalysts and they assist also in the formation of emulsions.

The hydrodeoxygenation of the fatty acids can be carried out at a temperature from 200 to 500° C., preferably from 280 to 400° C., under a pressure from 1 MPa to 10 MPa (10 to 100 bars), for example of 6 MPa, and with a hydrogen to refined oils ratio from 100 to 2000 Nl/l, for example of 600 Nl H2/l oil. The decarboxylation of the fatty acids can be carried out at 100 to 550° C. in absence or presence of hydrogen at pressures ranging from 0.01 up to 10 MPa.

Said refined oils can also be transformed into linear or substantially linear paraffin's as bio-naphtha by thermal decarboxylation of fatty acid soaps. These soaps are obtained during chemical refining by neutralisation to convert free fatty acids into soaps, by neutralisation of fatty acids obtained by hydrolysis of fats & oils or by complete saponification of triglycerides into glycerol and soap. A soap is a metal salt of the corresponding fatty acid.

The present invention also relates to the use of the bio-naphtha as obtained in the above mentioned process, as a direct feedstock of a steamcracker, said bio-naphtha being used as such, or together with the bio-propane when produced by the above-mentioned process, or as blended with at least a conventional feedstock selected among LPG, naphtha and gasoil, in order to obtain cracked products including bio-ethylene, bio-propylene, bio-butadiene, bio-isoprene, bio-(di)cyclopentadiene, bio-piperylenes, bio-benzene, bio-toluene, bio-xylene and bio-gasoline.

Moreover, the present invention relates to a process for steam cracking a feedstock as defined above, wherein said feedstock is mixed with steam, having a steam/feedstock ratio of at least 0.2 kg per kg of feedstock. This mixture is sent through the heated coils, having a coil outlet temperature of at least 700° C. and a coil outlet pressure of at least 1.2 bara.

DETAILED DESCRIPTION OF THE INVENTION

All crude fats & oils obtained after rendering, crushing or solvent extraction inevitably contain variable amounts of non-triglyceride components such as free fatty acids, mono and diglycerides, phosphatides, sterols, tocopherols, tocotrienols hydrocarbons, pigments (gossypol, chlorophyll), vitamins (carotenoids), sterols glucosides, glycolipids, protein fragments, traces of pesticides and traces metals, as well as resinous and mucilaginous materials. The quantities of the non-glycerides vary with the oil source, extraction process, season and geographical source. Removal of the non-triglyceride components, which interfere with further processing and cause the oil to darken, foam, smoke, precipitate and develop off-flavours, is the objective of the refining process.

Refining Pretreatment

Choice of the Refining Method

Figure 1:
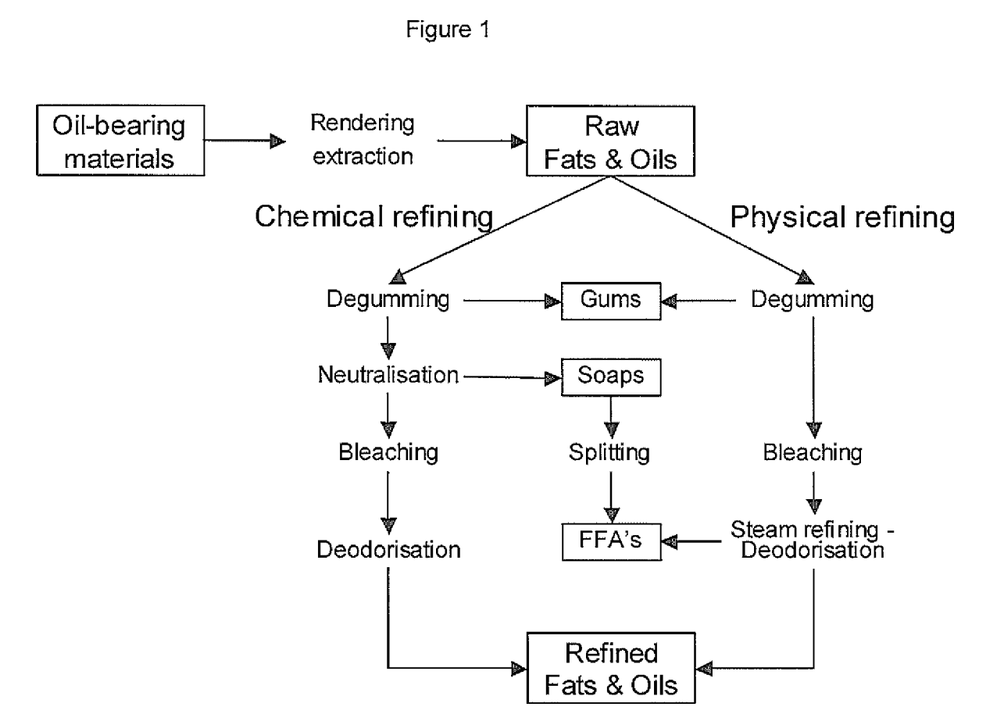
FIG. 1 illustrates a refining pretreatment in which crude oils are processed through various routes, physical or chemical, to Refined Bleached Deodorized (RBD) oils.

FIG. 1 illustrates the refining pretreatment in which crude oils are processed through various routes, physical or chemical, to Refined Bleached Deodorized (RBD) oils. Physical refining and alkali/chemical refining differ principally in the way free fatty acids are removed.

In chemical refining, FFA, most of the phosphatides, and other impurities are removed during neutralization with an alkaline solution, usually NaOH.

In physical refining, the FFA is removed by distillation during deodorization and the phosphatides and other impurities must be removed prior to steam distillation of fats & oils Currently, the refining method of choice is determined by the characteristics of the individual crude fats & oils:

(1) fats and oils that are normally physically refined;
(2) fats and oils that can be physically or chemically refined; and
(3) fats and oils that can only be chemically refined.

Table 2 below summarizes advantages and disadvantages of each treatment:

TABLE 2

| Refining type | Advantages | Disadvantages |
| --- | --- | --- |
| Chemical refining | Functional process | Production of by-products |
|  | Not restricted by the oil type | Expensive process |
|  | Successful reduction of FFA | High loss of oil |
| Physical refining | Cheaper | Not suitable for all types of oils |
|  | Less by-products | Requires high temperature and vacuum |
|  | Less energy consumed | Can form undesired side reaction products |

Physical Refining

The physical refining can remove the FFA, as well as the unsaponifiables and other impurities by steam stripping, thus eliminating the production of soapstock and keeping neutral oil loss to a minimum. However, degumming pretreatments of the crude fats & oils are still required to remove those impurities that darken or otherwise cause a poor-quality product when heated to the temperature required for steam distillation. A degumming process is crucial for physical refining but optional for chemical refining. It consists of the treatment of crude oils, with water, salt solutions, enzymes, caustic soda, or diluted acids such as phosphoric, citric or maleic to remove phosphatides, waxes, pro-oxidants and other impurities. The degumming processes convert the phosphatides to hydrated gums, which are insoluble in oil and readily separated as a sludge by settling, filtering or centrifugal action. After degumming, phosphorous must be less than 30 ppm. So that bleaching or dry degumming can further reduce this level to less than 5 ppm and remove all traces of iron and copper. Acid or enzymatic degumming processes are normally employed to achieve these results.

The various industrial degumming processes have different aims. Fats & oils to be degummed vary widely in gum content and gum properties and finally, the means of gum disposal available, what equipment is needed and/or available, and the cost of auxiliaries also influence the choice of the most appropriated degumming process. The lipid handbook (The lipid handbook, edited by Frank D. Gunstone, John L. Harwood, Albert J. Dijkstra. 3rd ed., chapter 3.4) deals with these aspects in details. Next is briefly described the four major degumming process applied on the market.

The main purposes of the water degumming process are to produce oil that does not deposit a residue during transportation and storage, and to control the phosphorus content of crude oils just below 200 ppm. This process involves the addition of live steam to raw oil for a short period. The proper amount of water is normally about 75% of the phosphatides content of the oil. Too little water produces dark viscous gums and hazy oil, while too much water causes excess oil losses through hydrolysis. Water-degummed oil still contains phosphatides (between 80 and 200 ppm); only hydratable phosphatides are removed with this process. The nonhydratable phosphatides, which are calcium and magnesium salts of phosphatic acid and phosphatidyl ethanolamine, remain in the oil after water degumming.

Acid degumming process leads to a lower residual phosphorus content than water degumming and is therefore a good alternative if dry degumming and physical refining are to be the next refining steps. The acid degumming process might be considered as a variant of the water degumming process in that it uses a combination of water and acid. The non-hydratable phosphatides can be conditioned into hydratable forms with acid degumming. Phosphoric and citric acids are used because they are food grade, sufficiently strong and they bind divalent metal ions. Several acid degumming processes have been developed to attain a phosphorus value lower than 5 ppm that is required for good quality physically refined oils.

An acid refining differs from the acid degumming by the neutralisation of the liberated phosphatides (the action of the degumming acid does not lead to full hydration of the phosphatides) to make them hydratable by the addition of a base.

In dry degumming process, the oil is treated with an acid (principle is that strong acids displace weaker acids from their salts) to decompose the metal ion/phosphatides complex and is then mixed with bleaching earth. The earth containing the degumming acid, phosphatides, pigments and other impurities is then removed by filtration. Seed oils that have been water or acid-degummed may also be dry degummed to ensure a low phosphorus oil to steam distillation. An increase in FFA of less than 0.2% should be expected but the final phosphorus content must be reduced to less than 5 ppm. This process constitutes the main treatment for palm oil, lauric oils, canola oil and low phosphatides animal fats, such as tallow or lard. The dry degumming process allows crude oil to be fully refined in only two steps: dry degumming and physical refining.

In enzymatic degumming process, Phospholipase A1, the lastest developed degumming enzyme, changes the phospholipids into lysophospholipids and free fatty acids. This process has three important steps:

(1) adjustment of the pH with a buffer;
(2) enzymatic reaction in the holding tanks; and
(3) separation of the sludge from the oil.

Oil to be degummed enzymatically by this way can be crude or water degummed.

The lipid handbook (The lipid handbook, edited by Frank D. Gunstone, John L. Harwood, Albert J. Dijkstra. 3rd ed.) describes many variants and details of the degumming processes.

The purpose of bleaching is to provide a decolored oil but also to purify it in preparation for further processing. All fully refined oils have been subjected to one or the other bleaching process. Refined oil contains traces of a number of undesirable impurities either in solution or as colloidal suspensions. The bleaching process does more than just increasing the transmission of light through the oil and is often called "adsorptive cleaning". The bleaching process is often the first filtration encountered by the oil, so it ensures the removal of soaps, residual phosphatides, trace metals, and some oxidation products, and it catalyses the decomposition of carotene and the adsorbent also catalyses the decomposition of peroxides. These non-pigment materials, such as soap, gums, and pro-oxidants metals, which hinder filtration, poison hydrogenation catalyst, darken the oils, and affect finished oil flavour. Another function is the removal of the peroxides and secondary oxidation products. The key parameters for the bleaching process are procedure, adsorbent type and dosage, temperature, time, moisture and filtration, as shown in the Lipid Handbook (The lipid handbook, edited by Frank D. Gunstone, John L. Harwood, Albert J. Dijkstra. 3rd ed., chapter 3.7). The three most common types of contact bleaching methods used for edible fats and oils are batch atmospheric, batch vacuum and continuous vacuum. Chemical agents have been used or proposed for use but practically all edible oil decoloration and purification is accomplished with adsorptive clays, synthetic amorphous silica and activated carbons.

Before the last major processing step, bleached oil can be hydrogenated, for two reasons. One reason is to change naturally occurring fats & oils into physical forms with the consistency and handling characteristics required for functionality. The second reason for hydrogenation is to increase the oxidation and thermal stability. Instead of purification in other described processes, this step consists in fats & oils molecular modification.

Hydrogen is added directly to react with unsaturated oil in the presence of catalysts, mostly nickel. This process greatly influences the desired stability and properties of many edible oil products. The hydrogenation process is easily controlled and can be stopped at any point. A gradual increase in the melting point of fats and oils is one of the advantages. If the double bonds are eliminated entirely with hydrogenation, the product is a hard brittle solid at room temperature. Shortening and margarine are typical examples. A wide range of fats and oils products can be produced with the hydrogenation process depending upon the conditions used, the starting oils, and the degree of saturation or isomerization.

To obtain good-quality fats and oils with physical refining, it is advantageous to have a phosphorous content lower than 5 ppm before steam stripping.

The degummed-bleached oils are vacuum stripped. This process encompasses the deodorization process, applied after the alkali routes, as well as physical refining. Deodorization, the last major processing step during which the FFA can be removed, is a vacuum-steam distillation process (1-2 mbar of residual pressure) at elevated temperature (180-240° C.) during which FFAs and minute levels of odoriferous materials, mostly arising from oxidation, are removed to obtain a bland and odorless oil. In order to volatilize the undesired high-boiling components, a deep vacuum and dilution with steam is applied so that the boiling temperature can be minimised. The deodorization utilizes the differences in volatility between off-flavour and off-odor substances and the triglycerides.

The odoriferous substances, FFAs, aldehydes, ketones, peroxides, alcohols, and others organic compounds are concentrated in a deodorizer distillate. Efficient removal of these substances depends upon their vapour pressure, for a given constituent is a function of the temperature and increases with the temperature.

As usually the last stage in the refining process, deodorization has an important effect an overall refined oil quality and distillate composition. Its main purposes are giving a bland taste and smell, low FFA content, high oxidative stability and light and stable colour. Because of the need of a rather high temperature to remove the undesired components, unwanted side effects are, isomerisation of double bond, polymerisation, intra-esterification and degradation of vitamins and antioxidants. New dry condensing (steam is condensed into ice) vacuum systems capable of reaching a very low operating pressure in the deodorizer were introduced (close to 0.1 kPa). This progress allows a reduction of the deodorization temperature without affecting the stripping efficiency in a negative way. In order to minimise the time that the oil is at high temperature, deodorizers can operate at dual temperatures to reach the best compromise between required residence time for deodorizing (at moderate temperature) and heat bleaching and final stripping at high temperature.

Deodorizer distillate is the material collected from the steam distillation of edible oils. The distillate from physically refined oils consists mainly of FFAs with low levels of unsaponifiable components. The concentration of FFA can be improved from typical 80% up to 98% by applying double condensing system that produces an enriched FFA cut. The distillate can be used as a source of industrial fatty acids or mixed with the fuel oil used to fire the steam boilers.

A physical refining will be preferred due to higher remaining FFA content in refined oils before steam stripping.

Chemical Refining

As applied to crude oils, it includes degumming (removal of phospholipids), neutralization (removal of free fatty acids), bleaching (decolorization) and deodorization (FIG. 1).

Degumming involves for instance the addition of water to hydrate any gums present, followed by centrifugal separation. Non-hydratable gums are removed by converting them first to a hydratable form using phosphoric or citric acid, followed by the addition of water and centrifugation. Acid degumming can also be used (see the description above).

The following step is neutralisation in which an aqueous alkali, typically caustic soda or sodium carbonate, is sprayed into the oil which has been preheated to around 75-95° C. The alkali reacts with free fatty acids in the oil to form soaps, which are separated by settling or centrifugation. Selection of the aqueous alkali strength, mixing time, mixing energy, temperature, and the quantity of excess caustic all have an important impact on making the chemical refining process operate efficiently and effectively. A drying step may be incorporated after neutralisation to ensure the complete removal of the added water. The soap can be used as such or can be hydrolysed (acidulation) with sulphuric acid into the corresponding FFA.

The neutralised oil is bleached to remove colouring matter (such as carotenoids) and other minor constituents, such as oxidative degradation products or traces of metals. Bleaching uses activated fuller's earth with treatments typically in the 90-130° C. range for 10-60 minutes. The earth is sucked into the oil under vacuum and is removed by filtration.

The bleached oil is steam distilled at low pressure to remove volatile impurities including undesirable odours and flavours. This process, known as deodorization, takes place in the temperature range of 180-270° C. and may last 15 minutes to five hours depending upon the nature of the oil, the quantity, and the type of equipment used.

Obtention of Bio-Naphtha from Refined Oils

Three options exist to convert fats & oils into LPG and naphtha-like hydrocarbons that can be used for the steam-cracking in order to produce light olefins, dienes and aromatics.

These are summarized in table 3.

TABLE 3

| Feedstock | Process | Catalyst/intermediate compounds |
|---|---|---|
| Triglycerides, eventually containing fatty acids | Catalytic Hydrodeoxygenation | Supported Ni, Mo, Co, NiW, NiMo, CoMo, NiCoW, NiCoMo, NiMoW and CoMoW oxides or sulphides |
| Fatty acids | Catalytic Decarboxylation | Supported group 10 (Ni, Pt, Pd) or group 11 (Cu, Ag) metals or alloys Basic oxides or mixed basic oxides |
| Fatty acids Soaps | Thermal Decarboxylation | Soaps of alkali, alkaline earth, lanthanides or group 12 or 13 |

The first option consists in hydrodeoxygenation, which removes the oxygen atoms from the fats & oils. This can be done on the triglycerides as such, the triglycerides containing FFA's or on only FFA's. Hydrodeoxygenation of fats & oils has been reported in 1989 (W. H. Craig and D. W. Soveran, "Production of hydrocarbons with relatively high cetane rating", U.S. Pat. No. 4,992,605 and Gusmao J, Brodzki D, Djega-Mariadassou G, Frety R., "Utilization of vegetable oils as an alternative source for diesel-type fuel: Hydrocracking on reduced Ni/SiO2 and sulphided Ni—Mo/γ-Al2O3", Cat. Today 1989 (5) 533) in which conventional CoMo or NiMo sulphided catalysts are used. These catalysts are well known in hydrodesulphurization and are known to catalyze also hydrodeoxygenation (E. Furimsky, Applied Catalysis A, General, 199, pages 147-190, 2000).

Hydrodeoxygenation of fats & oils is preferentially done in continuous fixed bed reactors, continuous stirred tank reactors or slurry type reactors containing solid catalyst that can be selected among Ni, Mo, Co or mixtures like NiW, NiMo, CoMo, NiCoW, NiCoMo, NiMoW and CoMoW oxides or sulphides as catalytic phase, preferably supported on high surface area carbon, alumina, silica, titania or zirconia. It is preferred that the support for the catalytic active phase exhibit low acidity, preferable neutral or basic in order to avoid hydro-isomerisation reactions that would result in branched paraffin's and cracking at elevated temperature and pressure in the presence of hydrogen. Temperature ranges from 200 to 500° C., pressure from 1 MPa to 10 MPa (10 to 100 bars) and hydrogen to oil feed ratio from 100 to 2000 Nm$^3$/m$^3$ of liquid. For optimum performance and stable continuous operation, it is preferred that the active metal component of the catalyst is in the form of sulfides. Thereto, it is preferred that traces amounts of decomposable sulphur compounds are present or added on purpose to the feedstock in order to keep the metal sulphide in its sulphide state. By way of example, these sulphur compounds can be $H_2S$, COS, $CS_2$, mercaptans (e.g. methylsulfide), thio-ethers (e.g. DiMethylSulfide), disulfides (e.g. DiMethyldiSulfide), thiophenic and tetrahydrothiophenic compounds.

Under hydrodeoxygenation conditions several reactions occur. The easiest is the hydrogenation of the double bonds in the alkyl-chain. The more difficult reaction is the removal of oxygen atoms from the C—O bonds. Both the carboxyl-group of the fatty acid as the hydroxyl-group of the glycerol-moiety are hydrodeoxygenated. This results in the production of linear paraffin, resulting from the fatty acid and in propane, resulting from glycerol. Depending on the conditions (catalyst, temperature, hydrogen etc), the carboxyl-group can also be decomposed into $CO/CO_2$ (decarboxylation) and which on their turn can be even further hydrogenated into methane. These hydrodeoxygenation reactions consume a lot of hydrogen.

As way of example is given the equation for triolein hydrodeoxygenation:

Hydrodeoxygenation of fatty acids:

Further hydrogenation of the intermediate $CO/CO_2$ can occur depending on the amount of available hydrogen, the catalyst and the operating conditions:

The second option consists in decarboxylation or decarbonylation of fatty acids. These fatty acids can be obtained from fats & oils by physical refining (including steam/vacuum distillation), by (steam) splitting of triglycerides or by splitting of soaps (acidulation) using acids. Decarboxylation of carboxylic acids has been reported in 1982 (W. F. Maier, Chemische Berichte, 115, pages 808-812, 1982) over Pd/SiO$_2$ and Ni/Al$_2$O$_3$ catalysts in the gas phase. A highly selective decarboxylation has been reported in 2005 (I. Kubickova, Catalysis Today, 106, pages 197-200, 2005 and M. Snare, Industrial Engineering, Chemistry Research, 45, p. 5708-5715, 2006) using transition metal catalysts. Palladium based catalysts exhibit the highest selectivity towards decarboxylation. Carboxylic acids can also be decarboxylated under catalytic conditions using basic catalyst, like MgO, ZnO and mixed basic oxides (A. Zhang *, Q. Ma, K. Wang, X. Liu, P. Shuler, Y. Tang, "Naphthenic acid removal from crude oil through catalytic decarboxylation on magnesium oxide", Applied Catalysis A: General 303, p. 103, 2006; A. More, John R. Schlup, and Keith L. Hohn "Preliminary Investigations of the Catalytic Deoxygenation of Fatty Acids", AIChe, The 2006 annual meeting, San Francisco and 13. Kitiyanan, C. Ung-jinda, V. Meeyoo, "Catalytic deoxygenation of oleic acid over ceria-zirconia catalysts", AIChe The 2008 annual meeting).

The following reactions can occur:
Decarboxylation:

$$R-CH_2-CH_2-COOH \rightarrow R-CH_2-CH_3+CO_2$$

Decarbonylation:

$$R-CH_2-CH_2-COOH \rightarrow R-CH=CH_2+CO+H_2O$$

Decarboxylation is preferentially done in presence of solid catalyst in batch type tank reactors, continuous fixed bed type reactors, continuous stirred tank reactors or slurry type reactors. The catalyst can be selected among Ni, Mo, Co or mixtures like NiW, NiMo, CoMo, NiCoW, NiCoMo, NiMoW and CoMoW oxides or sulphides as catalytic phase, preferably supported on high surface area carbon, alumina, silica, titania or zirconia or group 10 (Ni, Pt and Pd) and group 11 (Cu and Ag) metals or alloy mixtures supported on high surface area carbon, magnesia, zinc-oxide, spinels ($Mg_2Al_2O_4$, $ZnAl_2O_4$), perovskites ($BaTiO_3$, $ZnTiO_3$), calciumsilicates (like xonotlite), alumina, silica or silica-alumina's or mixtures of the latter. It is preferred that the support for the catalytic active phase exhibit low acidity, preferable neutral or basic in order to avoid hydro-isomerisation reactions that would result in branched paraffin's and cracking. Decarboxylation can also be carried out on basic oxides, like alkaline oxides, alkaline earth oxides, lanthanide oxides, zinc-oxide, spinels ($Mg_2Al_2O_4$, $ZnAl_2O_4$), perovskites ($BaTiO_3$, $ZnTiO_3$), calciumsilicates (like xonotlite), either as bulk material or dispersed on neutral or basic carriers, on basic zeolites (like alkali or alkaline earth low silica/alumina zeolites obtained by exchange or impregnation).

Although, the decarboxylation reaction does not require hydrogen, it is preferred that the decarboxylation is done in presence of hydrogen that will stabilise the catalytic activity by removing strongly adsorbed unsaturated species (for instance when decarbonylation is the prevalent reaction pathway) from the catalyst surface by hydrogen-addition reactions. The presence of hydrogen can also hydrogenate the double bonds present in the acyl-moiety of the fatty acid in order to obtain paraffinic reaction products from the decarboxylation process. The decarboxylation of the fatty acids can be carried out at 100 to 550° C. in absence or presence of hydrogen at pressures ranging from 0.01 up to 10 MPa. The hydrogen to feedstock ratio is from 0 to 2000 Nl/l.

Other reactions that can occur under the decarboxylation conditions are:

$$R-CH=CH_2+H_2 \rightarrow R-CH_2-CH_3$$

Hydrodeoxygenation of fatty acids:

$$R-CH_2-CH_2-COOH+3H_2 \rightarrow R-CH_2-CH_2 \rightarrow CH_3+2H_2O$$

Further hydrogenation of the intermediate $CO/CO_2$ can occur depending on the amount of available hydrogen, the catalyst and the operating conditions:

$$CO_2+4H_2 \rightarrow CH_4+H_2O$$

$$CO_2+4H_2 \rightarrow CH_4+2H_2O$$

A third option to obtain bio-naphtha from fats & oils is through the thermal decarboxylation of soaps of fatty acids. The soaps can be obtained from the chemical refining of fats & oils by neutralisation, producing refined triglycerides and soaps, by neutralisation of fatty acids obtained after (steam) splitting of fats & oils or by direct saponification of fats & oils using basic oxides or basic hydroxides, producing a soap and glycerol.

Decarboxylation has been carried out by decomposition of fatty acids in hot compressed water with the aid of alkali-hydroxides, resulting in the production of alkanes and $CO_2$ (M. Watanabe, Energy Conversion and Management, 47, p. 3344, 2006). Calcium-soaps of Tung oil have been reported to decompose by distillation as early as 1947 (C. C, Chang, S. W, Wan, "China's Motor Fuels from Tung Oil", Ind. Eng. Chem., 39 (12), p. 1543, 1947; Hsu, H. L., Osburn, J. O., Grove, C. S., "Pyrolysis of the calcium salts of fatty acids", Ind. Eng. Chem. 42 (10), p. 2141, 1950; Craveiro, A. A.; Matos, F. J. A.; Alencar, J. W.; Silveira E. R. Energia: Fontes Alternativas 3, p. 44, 1981; A. Demirbas, "Diesel fuel from vegetable oil via transesterification and soap pyrolysis", Energy Sources 24 9, p. 835, 2002).

The preferred soaps are those made of alkaline, alkaline earth, lanthanide, zinc or aluminium cations. The thermal decarboxylation of soap can be carried out by heating until the molten soap starts to decompose into the corresponding paraffin's or olefins and the corresponding metal-carbonate or metal-oxide/hydroxide and $CO_2$. Without willing to be bound to any theory, it is believed that the following overall reactions occur:

$$[R-CH_2-CH_2-COO^-]_xM^{x+}+xH_2O \rightarrow xR-CH_2-CH_3+M[HCO_3]_x$$

$$M[HCO_3]_x \leftarrow \rightarrow M[OH]_x+CO_2$$

It is preferred that the thermal decomposition of the soaps is carried out in the presence of liquid, supercritical or vaporous water.

Steamcracking

Steamcrackers are complex industrial facilities that can be divided into three main zones, each of which has several types of equipment with very specific functions: (i) the hot zone including: pyrolysis or cracking furnaces, quench exchanger and quench ring, the columns of the hot separation train (ii) the compression zone including: a cracked gas compressor, purification and separation columns, dryers and (iii) the cold zone including: the cold box, de-methaniser, fractionating columns of the cold separation train, the $C_2$ and $C_3$ converters, the gasoline hydrostabilization reactor Hydrocarbon cracking is carried out in tubular reactors in direct-fired heaters (furnaces). Various tube sizes and configurations can be used, such as coiled tube, U-tube, or straight tube layouts. Tube diameters range from 1 to 4 inches. Each furnace consists of a convection zone in which the waste heat is recovered and a radiant zone in which pyrolysis takes place. The feedstock-steam mixture is preheated in the convection zone to about 530-650° C. or the feedstock is preheated in the convection section and subsequently mixed with dilution steam before it flows over to the radiant zone, where pyrolysis takes place at temperatures varying from 750 to 950° C. and residence times from 0.05 to 0.5 second, depending on the feedstock type and the cracking severity desired. In an advantageous embodiment the residence time is from 0.05 to 0.15 second. The steam/feedstock (the steam/[hydrocarbon feedstock]) weight ratio is between 0.2 and 1.0 kg/kg, preferentially between 0.3 and 0.5 kg/kg. In an advantageous embodiment the steam/feedstock weight ratio is between 0.2 and 0.45 and preferably between 0.3 and 0.4. For steamcracking furnaces, the severity can be modulated by: temperature, residence time, total pressure and partial pressure of hydrocarbons. In general the ethylene yield increases with the temperature while the yield of propylene decreases. At high temperatures, propylene is cracked and hence contributes to more ethylene yield. The increase in severity thus obtained leads to a moderate decrease in selectivity and a substantial decrease of the ratio $C_3=/C_2=$. So high severity operation favors ethylene, while low severity operation favors propylene production. The residence time of the feed in the coil and the temperature are to be considered together. Rate of coke formation will determine maximum acceptable severity. A lower operating pressure results in easier light olefins formation and reduced coke formation. The lowest pressure possible is accomplished by (i) maintaining the output pressure of the coils as close as possible to atmospheric pressure at the suction of the cracked gas compressor (ii) reducing the pressure of the hydrocarbons by dilution with steam (which has a substantial influence on slowing down coke formation). The steam/feed ratio must be maintained at a level sufficient to limit coke formation.

Effluent from the pyrolysis furnaces contains unreacted feedstock, desired olefins (mainly ethylene and propylene), hydrogen, methane, a mixture of $C_4$'s (primarily isobutylene and butadiene), pyrolysis gasoline (aromatics in the $C_6$ to $C_8$ range), ethane, propane, di-olefins (acetylene, methyl acetylene, propadiene), and heavier hydrocarbons that boil in the temperature range of fuel oil. This cracked gas is rapidly quenched to 338-510° C. to stop the pyrolysis reactions, minimize consecutive reactions and to recover the sensible heat in the gas by generating high-pressure steam in parallel transfer-line heat exchangers (TLE's). In gaseous feedstock based plants, the TLE-quenched gas stream flows forward to a direct water quench tower, where the gas is cooled further with recirculating cold water. In liquid feedstock based plants, a prefractionator precedes the water quench tower to condense and separate the fuel oil fraction from the cracked gas. In both types of plants, the major portions of the dilution steam and heavy gasoline in the cracked gas are condensed in the water quench tower at 35-40° C. The water-quench gas is subsequently compressed to about 25-35 Bars in 4 or 5 stages. Between compression stages, the condensed water and light gasoline are removed, and the cracked gas is washed with a caustic solution or with a regenerative amine solution, followed by a caustic solution, to remove acid gases ($CO_2$, $H_2S$ and $SO_2$). The compressed cracked gas is dried with a desiccant and cooled with propylene and ethylene refrigerants to cryogenic temperatures for the subsequent product fractionation: Front-end demethanization, Front-end depropanization or Front-end deethanization.

In a front-end demethanization configuration, tail gases (CO, $H_2$, and $CH_4$) are separated from the $C_2$+ components first by de-methanization column at about 30 bars. The bottom product flows to the de-ethanization, of which the overhead product is treated in the acetylene hydrogenation unit and further fractionated in the $C_2$ splitting column. The bottom product of the de-ethanization goes to the de-propanization, of which the overhead product is treated in the methyl acetylene/propadiene hydrogenation unit and further fractionated in the $C_3$ splitting column. The bottom product of the de-propaniser goes to the de-butanization where the $C_4$'s are separated from the pyrolysis gasoline fraction. In this separation sequence, the $H_2$ required for hydrogenation is externally added to $C_2$ and $C_3$ streams. The required $H_2$ is typically recovered from the tail gas by methanation of the residual CO and eventually further concentrated in a pressure swing adsorption unit.

Front-end de-propanization configuration is used typically in steamcrackers based on gaseous feedstock. In this configuration, after removing the acid gases at the end of the third compression stage, the $C_3$ and lighter components are separated from the $C_{4+}$ by de-propanization. The de-propanizer $C_3$– overhead is compressed by a fourth stage to about 30-35 bars. The acetylenes and/or dienes in the $C_3$– cut are catalytically hydrogenated with $H_2$ still present in the stream. Following hydrogenation, the light gas stream is de-methanized, de-ethanized and $C_2$ split. The bottom product of the de-ethanization can eventually be $C_3$ split. In an alternative configuration, the $C_3$– overhead is first de-ethanized and the $C_2$– treated as described above while the $C_3$'s are treated in the $C_3$ acetylene/diene hydrogenation unit and $C_3$ split. The $C_4$+ de-propanizer bottom is de-butanized to separate $C_4$'s from pyrolysis gasoline. There are two versions of the front-end de-ethanization separation sequence. The product separation sequence is identical to the front-end de-methanization and front-end depropanization separation sequence to the third compression stage. The gas is de-ethanized first at about 27 bars to separate $C_2$– components from $C_3$+ components. The overhead $C_2$– stream flows to a catalytic hydrogenation unit, where acetylene in the stream is selectively hydrogenated. The hydrogenated stream is chilled to cryogenic temperatures and de-methanized at low pressure of about 9-10 bars to strip off tail gases. The $C_2$ bottom stream is split to produce an overhead ethylene product and an ethane bottom stream for recycle. In parallel, the $C_3$+ bottom stream from the front-end de-ethanizer undergoes further product separation in a de-propaniser, of which the overhead product is treated in the methyl acetylene/propadiene hydrogenation unit and further fractionated in the $C_3$ splitting column. The bottom product of the de-propaniser goes to the de-butanization where the $C_4$'s are separated from the pyrolysis gasoline fraction. In the more recent version of the front-end de-ethanization separation configuration, the cracked gas is caustic washed after three compression stages, pre-chilled and is then de-ethanized at about 16-18 bars top pressure. The net overhead stream ($C_2$–) is compressed further in the next stage to about 35-37 bars before it passes to a catalytic converter to hydrogenate acetylene, with hydrogen still contained in the stream. Following hydrogenation, the stream is chilled and de-methanized to strip off the tail gases from the $C_2$ bottom stream. The $C_2$'s are split in a low pressure column operating at 9-10 bars pressure, instead of 19-24 bars customarily employed in high pressure $C_2$ splitters that use a propylene refrigerant to condense reflux for the column. For the low-pressure $C_2$ splitter separation scheme, the overhead cooling and compression system is integrated into a heat-pump, open-cycle ethylene refrigeration circuit. The ethylene product becomes a purged stream of the ethylene refrigeration recirculation system.

The ethane bottom product of the $C_2$ splitter is recycled back to steam cracking. Propane may also be re-cracked, depending on its market value. Recycle steam cracking is accomplished in two or more dedicated pyrolysis furnaces to assure that the plant continues operating while one of the recycle furnaces is being decoked.

Many other variations exist of the above-described configurations, in particular in the way the undesired acetylene/dienes are removed from the ethylene and propylene cuts.

Figure 2:
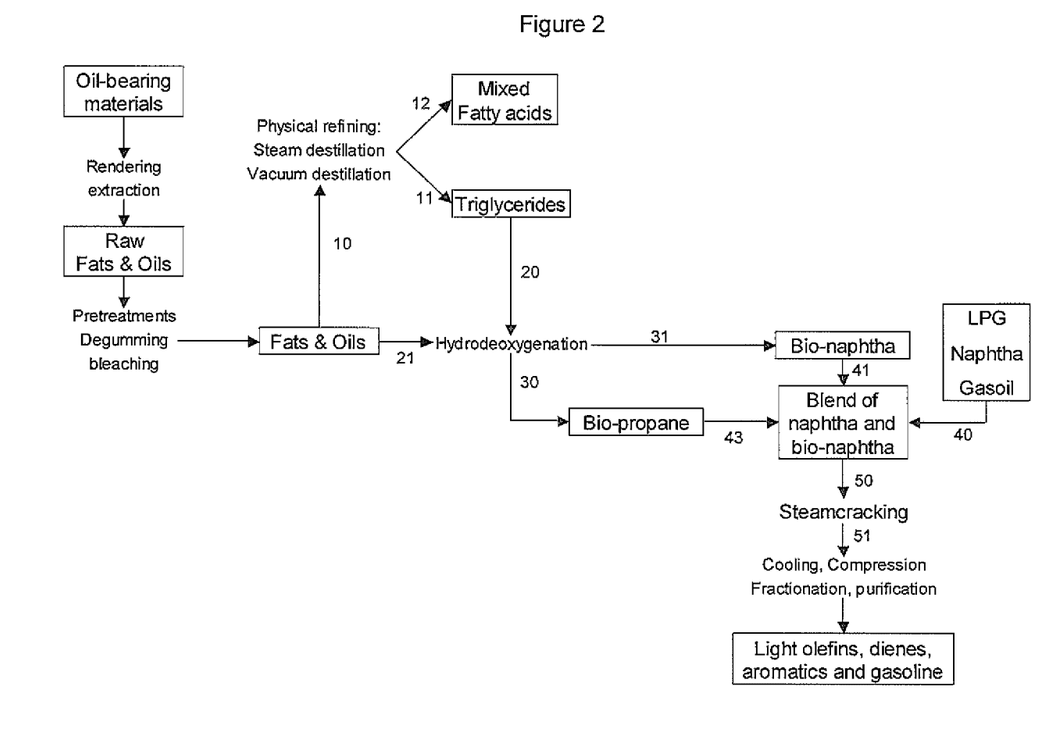
FIG. 2 illustrates physical refinement of fats and oils by vacuum distillation or steam distillation to recover mixed fatty acids as overhead product and the triglycerides as bottom product.
Figure 3:
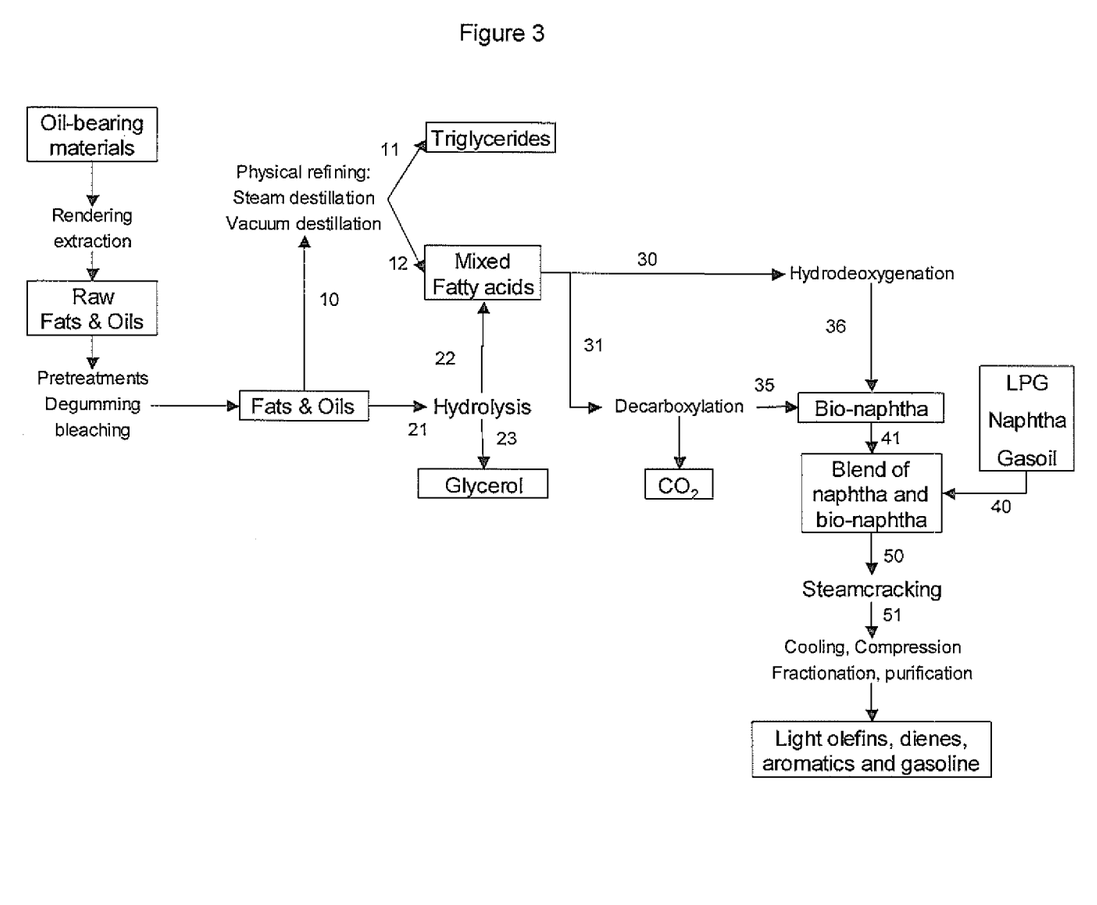
FIG. 3 illustrates another embodiment of physical refinement of fats and oils by vacuum distillation or steam distillation to recover mixed fatty acids as overhead product and triglycerides as bottom product.
Figure 4:
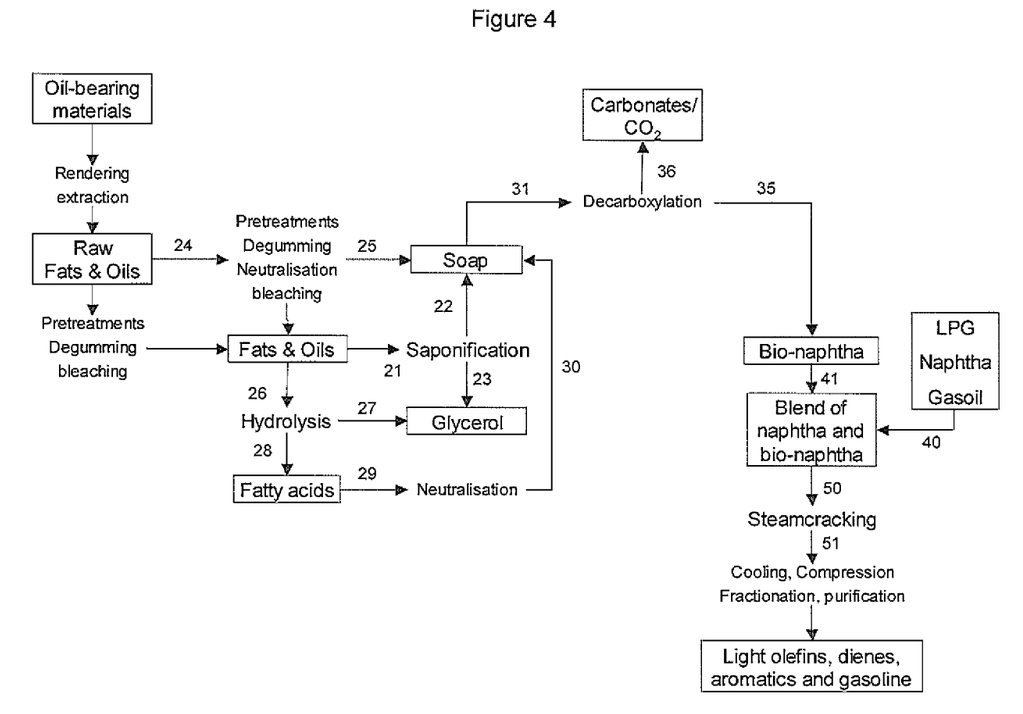
FIG. 4 illustrates saponification of fats and oils to recover soap and glycerol.

Various embodiments are represented in FIGS. 2 to 4.

In a first embodiment (FIG. 2), Fats & Oils are physically refined by vacuum distillation or steam distillation (10) to recover the mixed fatty acids (12) as overhead product and the triglycerides (11) as bottom product. Either the fats & oils, eventually still containing free fatty acids (21) or the physically refined triglycerides (20) acids can be sent to a hydrodeoxygenation section where they are converted into bio-naphtha (31) and bio-propane (30). This bio-naphtha (41) and bio-propane (43) are sent to the to steamcracking (50) or blended with fossil LPG, naphtha or gasoil (40) and hence the blend is streamcracked (50). The products of the steamcracking are cooled, compressed, fractionated and purified (51). This results in light olefins (ethylene, propylene and butenes), dienes (butadiene, isoprene, (di)cyclopentadiene and piperylenes), aromatics (benzene, toluene and mixed xylenes) and gasoline as main components.

In a second embodiment (FIG. 3), Fats & Oils are physically refined by vacuum distillation or steam distillation (10) to recover the mixed fatty acids (12) as overhead product and the triglycerides (11) as bottom product. Optionally fats & Oils can be hydrolysed (21) to produce mixed fatty acids (22) and glycerol (23). The quality of the mixed fatty acids can be further improved by hydrogenation of double bonds in the acyl-moiety or before hydrolysis, the fats & oils can be hydrogenated to remove the remaining double bonds and subsequently sent (21) to the hydrolysis step. The mixed fatty acids can be sent (30) to a hydrodeoxygenation section where they are converted into bio-naphtha (36) or alternatively they can be sent to the decarboxylation section (31) where they are converted into bio-naphtha (35). This bio-naphtha (41) is sent to the to steamcracking (50) or blended with fossil LPG, naphtha or gasoil (40) and hence the blend is streamcracked (50). The products of the steamcracking are cooled, compressed, fractionated and purified (51). This results in light olefins (ethylene, propylene and butenes), dienes (butadiene, isoprene, (di)cyclopentadiene and piperylenes), aromatics (benzene, toluene and mixed xylenes) and gasoline as main components.

In a third embodiment (FIG. 4), fats & Oils are saponificated (21) to recover the soap (22) and glycerol (23). Optionally fats & Oils can hydrolysed (21) to produce mixed fatty acids (22) and glycerol (23). Alternatively, soap (25) can be obtained during a chemical refining step of raw fats & oils (24) by the neutralisation step. Still another source of soap (30) is via neutralisation (29) of fatty acids, obtained by (steam) splitting (26) of fats & oils, producing fatty acids (28) and glycerol (27). The quality of the soaps can be further improved by hydrogenation of double bonds in the acyl-moiety or before saponification or hydrolysis, the fats & oils can be hydrogenated to remove the remaining double bonds and subsequently sent to the saponification (21) or hydrolysis (26) step. The soaps can be sent (31) to the decarboxylation section where they are converted into bio-naphtha (35) and metal-carbonates or $CO_2$ (36). This bio-naphtha (41) is sent to the to steamcracking (50) or blended with fossil LPG, naphtha or gasoil (40) and hence the blend is streamcracked (50). The products of the steamcracking are cooled, compressed, fractionated and purified (51). This results in light olefins (ethylene, propylene and butenes), dienes (butadiene, isoprene, (di)cyclopentadiene and piperylenes), aromatics (benzene, toluene and mixed xylenes) and gasoline as main components.

EXAMPLES

Example 1

Hydrodeoxygenation of a Triglyceride Feed has been Evaluated Under the Following Conditions In an isothermal reactor, 10 ml of a hydrotreating catalyst composed of Molybdenum and Nickel supported on alumina (KF848 obtained from Albemarle) was loaded, the catalyst dried and pre-sulfurized under standard conditions with straightrun gasoil doped with DMDS.

The hydrodeoxygenation of rapeseed is done at:
LHSV=1 $h^{-1}$
Inlet Temperature=320° C.
Outlet pressure=60 bars
H2/oil ratio=630 Nl/l
Feedstock=rapeseed doped with 1 wt % DMDS Table 4 shows a typical composition of the rapeseed oil.

The gas and liquid effluent are separated by means of a separator (gas/liquid) at atmospheric pressure. Gases are sent to a µ-GC analyser and liquids are sent to a sampler. The mass balance is around 99% and all product weights are calculated for 100 g of treated feed.

TABLE 4

Typical composition of rapeseed oil

| Components | wt % |
|---|---|
| tetradecanoate | 0.1 |
| hexadecenoate | 0.2 |
| hexadecanoate | 4.8 |
| heptadecanoate | 0.1 |
| octadecadienoate | 20.6 |
| octadecenoate | 61.3 |
| octadecatrienoate | 8.6 |
| octadecanoate | 1.8 |
| eisosenoate | 1.2 |
| eicosanoate | 0.7 |
| docosenoate | 0.3 |
| docosanoate | 0.3 |
| | 100 |

The total liquid effluent is biphasic and need a separation step. The organic phase was analyzed via GC-MS. A complete analysis is reported in table 5.

The liquid effluent is composed of 94.4 wt % of n-paraffins but it is composed of 99.94 wt % of interesting components, which could be sent to the naphtha-cracker.

TABLE 5

Material balance and complete GC analysis of hydrocarbon phase

| Feed | Products |
|---|---|
| 5.96 gr hydrogen | 6.48 gr CO2 |
| 100 gr rapeseed | 0.55 gr CO |
| | 3.52 H2 |
| | 5.98 gr propane |
| | 0.18 gr methane |
| | 2.77 gr water phase |
| | 85 gr hydrocarbon phase |

| Hydrocarbon phase composition | Wt % |
|---|---|
| C3 | 0.005 |
| n-paraffin's with $C_5$ to $C_{14}$ | 0.268 |
| other paraffin's with $C_5$ to $C_{14}$ | 0.238 |
| other C15 | 0.061 |
| n-C15 | 2.353 |
| other C16 | 0.100 |
| n-C16 | 2.754 |
| other C17 | 1.633 |
| n-C17 | 41.077 |
| other C18 | 2.108 |
| n-C18 | 44.344 |
| dodecyl-cyclohexane | 0.168 |
| tridecyl-cyclopentane | 0.110 |
| n-paraffin's with $C_{19}$ to $C_{35}$ | 3.599 |
| other paraffin's with $C_{19}$ to $C_{35}$ | 1.1 |
| >n-C35 | 0.013 |
| 2-butanone | 0.034 |
| Other oxygenates | 0.025 |
| Total | 100.00 |

94.4 wt % of the hydrocarbon phase are comprised of n-paraffin's that is high quality bio-naphtha feedstock for a steamcracker. About 0.059 wt % of remaining oxygenates are found in the hydrocarbon phase. That corresponds to 112 wppm O-atoms. Considering the 0 content in the triglyceride feed, that represents 10.86 wt % (or 108600 wppm O-atoms), resulting in a hydrodeoxygenation conversion of 99.89%.

Example 2 n-Paraffin's and conventional naphtha have been steam-cracked under different severity conditions. Table 6 gives the results. It is evident from the results that such-obtained bio-naphtha are better feedstock for steamcracking compared to fossil naphtha.

Significant higher ethylene and propylene yields can be obtained whereas the methane make and the pyrolysis gasoline make is reduced with at least about 20%. The ultimate yield of HVC (High value Chemicals=H2+ethylene+propylene+butadiene+benzene) is above 70 wt %. Ethylene/Methane weight ratio is always above 3.

TABLE 6

|  | Naphtha | n-Decane | n-C15 | n-C20 | Naphtha | n-Decane | n-C15 | n-C20 |
| --- | --- | --- | --- | --- | --- | --- | --- | --- |
| P/E | 0.59 | 0.44 | 0.50 | 0.49 | 0.50 | 0.39 | 0.44 | 0.44 |
| COT | 812 | 812 | 812 | 812 | 832 | 832 | 832 | 832 |
| S/HC | 0.35 | 0.35 | 0.35 | 0.35 | 0.35 | 0.35 | 0.35 | 0.35 |
| Summary | wt % (dry) | wt % (dry) | wt % (dry) | wt % (dry) | wt % (dry) | wt % (dry) | wt % (dry) | wt % (dry) |
| Hydrogen | 0.87 | 0.66 | 0.59 | 0.57 | 0.96 | 0.76 | 0.69 | 0.67 |
| Methane | 14.79 | 11.67 | 10.65 | 10.00 | 16.25 | 12.80 | 11.80 | 11.15 |
| Acetylene | 0.25 | 0.25 | 0.25 | 0.25 | 0.36 | 0.37 | 0.37 | 0.37 |
| Ethylene | 25.39 | 38.87 | 36.24 | 35.82 | 26.91 | 39.67 | 36.93 | 36.47 |
| Ethane | 4.09 | 6.58 | 6.07 | 5.84 | 3.89 | 6.10 | 5.62 | 5.42 |
| Methyl-Acetylene | 0.29 | 0.21 | 0.22 | 0.22 | 0.36 | 0.26 | 0.27 | 0.27 |
| Propadiene | 0.21 | 0.15 | 0.16 | 0.16 | 0.25 | 0.18 | 0.19 | 0.19 |
| Propylene | 15.10 | 17.29 | 18.08 | 17.63 | 13.48 | 15.59 | 16.28 | 15.91 |
| Propane | 0.51 | 0.73 | 0.69 | 0.66 | 0.44 | 0.62 | 0.59 | 0.57 |
| Vinyl-Acetylene | 0.04 | 0.04 | 0.04 | 0.04 | 0.05 | 0.06 | 0.07 | 0.07 |
| Butadiene | 4.61 | 5.96 | 6.88 | 7.30 | 4.41 | 5.79 | 6.49 | 6.79 |
| Butene (sum) | 4.86 | 2.99 | 3.34 | 3.43 | 3.67 | 2.12 | 2.34 | 2.38 |
| Butane (sum) | 0.08 | 0.14 | 0.12 | 0.12 | 0.06 | 0.11 | 0.09 | 0.09 |
| Total C5-C9's | 23.69 | 12.48 | 14.65 | 15.75 | 22.30 | 13.14 | 15.33 | 16.42 |
| Total C10+ | 5.17 | 1.93 | 1.96 | 2.15 | 6.53 | 2.38 | 2.86 | 3.18 |
| Carbon Oxide | 0.05 | 0.05 | 0.05 | 0.05 | 0.07 | 0.07 | 0.07 | 0.07 |
| Carbon Dioxide | 0.00 | 0.00 | 0.00 | 0.00 | 0.01 | 0.00 | 0.00 | 0.00 |
| Ultimate Ethylene | 28.67 | 44.14 | 41.09 | 40.49 | 30.02 | 44.55 | 41.43 | 40.80 |
| C2= + C3= | 43.77 | 61.43 | 59.17 | 58.12 | 43.51 | 60.14 | 57.71 | 56.70 |
| BENZENE | 8.27 | 5.35 | 6.46 | 7.05 | 9.42 | 6.55 | 7.77 | 8.39 |
| HVC's | 54.25 | 68.14 | 68.24 | 68.37 | 55.18 | 68.35 | 68.16 | 68.23 |
| Ultimate HVC's | 57.52 | 73.40 | 73.10 | 73.04 | 58.29 | 73.23 | 72.66 | 72.56 |

| Naphtha composition | wt % |
| --- | --- |
| Normal paraffins | 31.26 |
| Iso paraffins | 33.48 |
| Naphtenics | 28.1 |
| Aromatics | 7.16 |
| Olefins | 0 |
| Others | 0 |

P/E is the propylene/ethylene ratio
COT is the coil outlet temperature
S/HC is the ratio steam/hydrocarbon

What is claimed:

1. A process for making a bio-naphtha and optionally bio-propane from a complex mixture of natural occurring fats & oils, wherein
    said complex mixture is subjected to a refining treatment for removing a major part of non-triglyceride and non-fatty acid components, thereby obtaining refined fats & oils; and
    said refined fats & oils are transformed into linear or substantially linear paraffins as the bio-naphtha by hydrodeoxygenation; or
    from said refined fats & oils are obtained fatty acids that are transformed into linear or substantially linear paraffins as the bio-naphtha by hydrodeoxygenation or decarboxylation of free fatty acids; or
    from said refined fats & oils are obtained fatty acid soaps that are transformed into linear or substantially linear paraffins as the bio-naphtha by decarboxylation of the fatty acid soaps.

2. The process according to claim 1, wherein said complex mixture of natural occurring fats & oils is selected among vegetable oils and animal fats.

3. The process according to claim 1, wherein said fatty acids are obtained by physical refining, including a steam distillation or vacuum distillation of fats & oils;
    or said fatty acids are obtained by hydrolysis of triglycerides of the fats & oils;
    or said fatty acids are obtained by acidulation of soaps.

4. The process according to claim 1, wherein said fatty acid soaps are obtained by:
    saponification of fats & oils;
    or by the chemical refining, including neutralisation of free fatty acids, present in the fats & oils;
    or neutralisation of fatty acids, obtained from hydrolysis of the fats & oils.

5. The process according to claim 1, wherein said refined fats & oils are transformed into linear or substantially linear paraffins as bio-naphtha together with bio-propane by hydrodeoxygenation in the presence of hydrogen and at least one catalyst selected among Ni, Mo, Co, NiW, NiMo, CoMo, NiCoW, NiCoMo, NiMoW and CoMoW oxides or sulphides as catalytic phase, optionally supported on high surface area carbon, alumina, silica, titania or zirconia.

6. The process according to claim 5, wherein the hydrodeoxygenation is carried out at a temperature from 200 to 500° C., under a pressure from 1 MPa to 10 MPa and with a hydrogen to feed ratio from 100 to 2000 Nl/l.

7. The process according to claim 1, wherein said refined fats & oils are transformed into linear or substantially linear paraffins as bio-naphtha by hydrolysis of the fats & oils into glycerol and fatty acids, removal of the glycerol or by physical refining, including a steam distillation or vacuum distillation of fats & oils or obtained by acidulation of soaps and hydrodeoxygenation or decarboxylation of the fatty acids, said hydrodeoxygenation or decarboxylation being conducted in the presence of hydrogen and at least one catalyst selected among Ni, Mo, Co, NiW, NiMo, CoMo, NiCoW, NiCoMo, NiMoW and CoMoW oxides or sulphides as catalytic phase, optionally supported on high surface area carbon, alumina, silica, titania or zirconia or group 10 and group 11 metals or alloy mixtures supported on high surface area carbon, magnesia, zinc-oxide, spinels, perovskites, calciumsilicates, alumina, silica or silica-alumina's or mixtures of the latter.

8. The process according to claim 1, wherein said refined fats & oils are transformed into linear or substantially linear paraffins as bio-naphtha by hydrolysis of the fats & oils into glycerol and fatty acids, removal of the glycerol or by physical refining, including a steam distillation or vacuum distillation of fats & oils or obtained by acidulation of soaps and decarboxylation of the fatty acids is carried out on basic oxides, alkaline earth oxides, lanthanide oxides, zinc-oxide, spinels, perovskites, calciumsilicates, either as bulk material or dispersed on neutral or basic carriers, on basic zeolites.

9. The process according to claim 7, wherein the hydrodeoxygenation is carried out at a temperature from 200 to 500° C., under a pressure from 1 MPa to 10 MPa and with a hydrogen to feedstock ratio from 100 to 2000 Nl/l, or wherein the decarboxylation is carried out at a temperature from 100 to 550° C., under a pressure from 0.1 MPa to 10 MPa and with a hydrogen to feedstock ratio from 0 to 2000Nl/l.

10. The process according to claim 4, wherein the decarboxylation of the fatty acid soaps is carried out at from 100 to 550° C. under pressure from 0.1 Mpa to 10 Mpa and in presence of water.

11. The process according to claim 4, wherein the decarboxylation of the fatty acid soaps is carried out with a water to feedstock ratio of at least 1 mole water per mole of fatty acid soap.

12. The process according to claim 1, wherein said complex mixture of natural occurring fats & oils is selected among inedible oils, highly saturated oils, waste food oils, by-products of the refining of vegetable oils, and mixtures thereof.

13. The process according to claim 1, wherein the non-triglyceride and non-fatty acid components comprise free fatty acids.

\* \* \* \* \*